(12) United States Patent
Cogger et al.

(10) Patent No.: US 6,254,579 B1
(45) Date of Patent: Jul. 3, 2001

(54) MULTIPLE PRECISION DOSE, PRESERVATIVE-FREE MEDICATION DELIVERY SYSTEM

(75) Inventors: John J. Cogger, Irvine; David S. Haffner, Mission Viejo, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/435,703

(22) Filed: Nov. 8, 1999

(51) Int. Cl.$^7$ .................................................. A61M 35/00
(52) U.S. Cl. ........................ 604/298; 604/218; 604/256; 604/311
(58) Field of Search ..................................... 604/294, 295, 604/190, 218, 231, 256, 301, 298, 311, 19, 46, 48, 68, 70, 71, 72, 131, 150, 151, 152, 181, 183, 186, 187, 246, 249, 257, 275, 289

(56) References Cited

U.S. PATENT DOCUMENTS

| | | | |
|---|---|---|---|
| D. 368,774 | 4/1996 | Py | D24/110 |
| D. 374,719 | 10/1996 | Py | D24/120 |
| 4,792,334 | 12/1988 | Py | 604/301 |
| 4,908,024 | 3/1990 | Py | 604/300 |
| 4,946,452 | 8/1990 | Py | 604/301 |
| 4,981,479 | 1/1991 | Py | 604/302 |
| 5,085,651 | 2/1992 | Py | 604/298 |
| 5,133,702 | 7/1992 | Py | 604/302 |
| 5,163,929 | 11/1992 | Py | 604/298 |
| 5,267,986 | 12/1993 | Py | 604/294 |
| 5,320,845 | 6/1994 | Py | 424/427 |
| 5,401,259 | 3/1995 | Py | 604/294 |
| 5,499,751 | * 3/1996 | Meyer | 222/386 |
| 5,613,957 | 3/1997 | Py | 604/294 |
| 5,641,004 | 6/1997 | Py | 141/3 |
| 5,685,869 | * 11/1997 | Py | 604/294 |
| 5,730,723 | * 3/1998 | Castellano et al. | 604/68 |
| 5,746,728 | 5/1998 | Py | 604/298 |
| 5,855,322 | 1/1999 | Py | 239/11 |

* cited by examiner

Primary Examiner—Richard K. Seidel
Assistant Examiner—Jennifer Maynard
(74) Attorney, Agent, or Firm—Walter A. Hackler

(57) ABSTRACT

Apparatus for instilling a medicament into an eye includes a rigid housing for containing a reservoir of medicament and a nozzle for instilling a dose of the medicament into an eye. A displacement pump, sealing a front end of the rigid housing and in fluid communication with the reservoir, provides for metering doses of medicament from the reservoir to the nozzle and for forcing each metered dose through the nozzle. A stopper, slidably disposed within a rear end of the rigid housing, provides for gradually decreasing the housing volume containing the medicament reservoir. A diaphragm provides for accommodating transient decreases in the volume containing the medicament reservoir during metering of doses therefrom by the displacement pump.

37 Claims, 2 Drawing Sheets

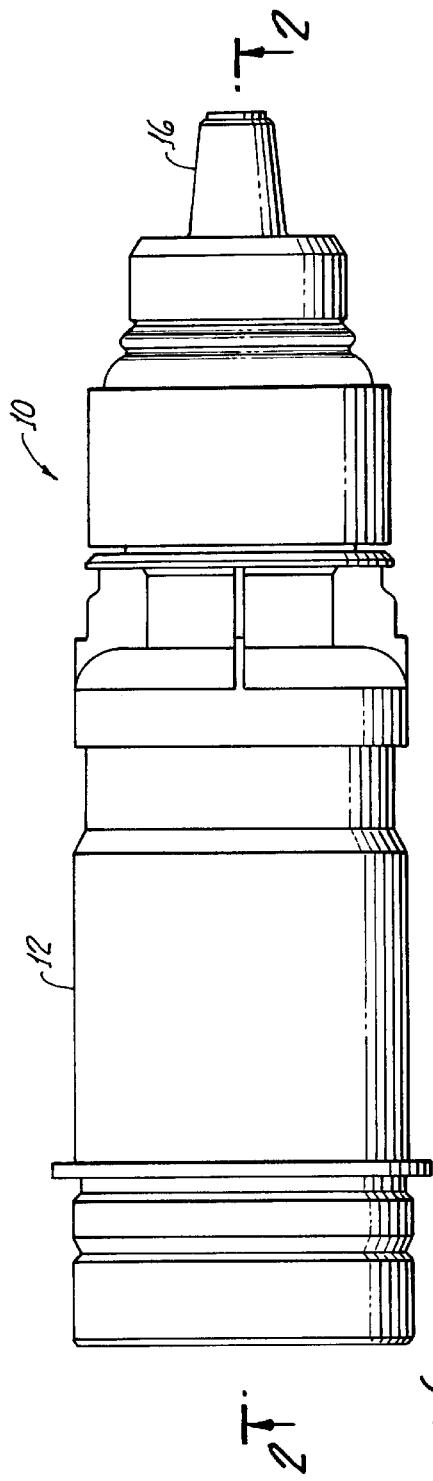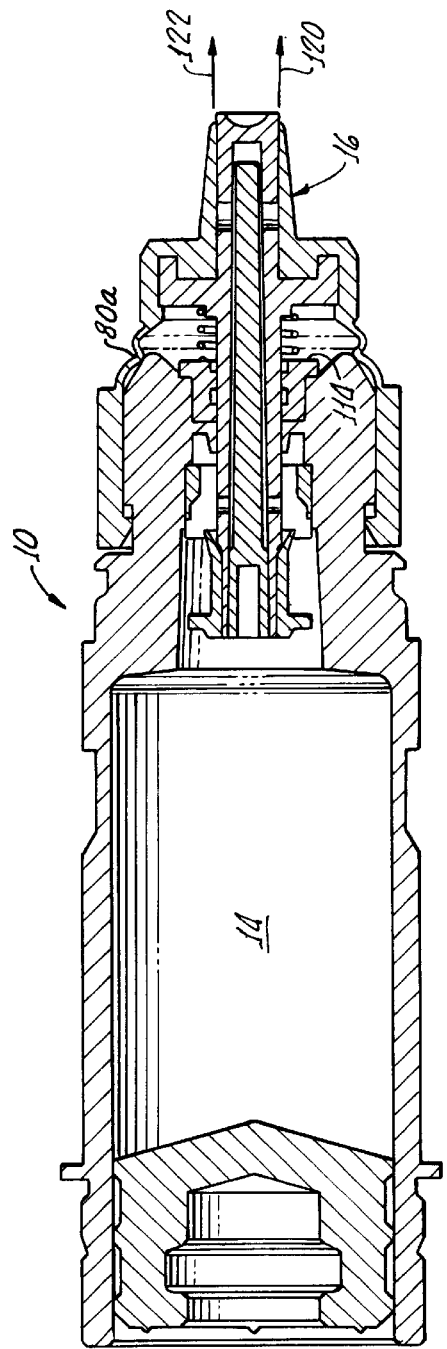

MULTIPLE PRECISION DOSE, PRESERVATIVE-FREE MEDICATION DELIVERY SYSTEM

The present invention generally relates to apparatus for dispensing microliter amounts of medicament and is more particularly directed to apparatus for instilling a medicament into an eye.

A great number of devices have been developed for instilling medicament to an eye. Well known eye drop containers conventionally include a squeezable container and a nozzle for releasing drops of medicament into the eye by compression of the container. Obviously, this apparatus affords no practical method of dispensing a measured dose of medicament inasmuch as the liquid dispensed from the nozzle is dependent upon the amount of compression of the container. Thus, there is no way of accurately controlling the volume of each dose of medicament released into the eye and, further, the smallest drop obtainable is the result of the combined effective gravity and surface tension.

When preservative-free medicaments are utilized, simple eye drop dispensers are not practical because there are no means for preventing the tip from being contaminated due to its exposure to air. Such tip contamination ultimately spreads to the medicament in the container.

In an attempt to overcome these problems, apparatus has been developed for applying a medicament to an eye which includes a nozzle having a seam which is normally in a closed position for preventing the passage of medicament through the nozzle, and which opens in response to a flow of medicament of sufficient pressure to enable opening of the seam in order to permit the passage of medicament through the nozzle for release into the eye, see U.S. Pat. No. 5,685,869.

While this nozzle is suitable, there is difficulty in coupling the nozzle with a suitable reservoir of medicament in order to create a working, producible device for multiple dose delivery of a preservative-free product of sufficient dose accuracy for consumer benefit and regulatory body registration over an extended period of time of up to six months or more.

Operation of prior art devices such as set forth in the hereinabove referenced U.S. patent, typically causes a small negative pressure, or vacuum, within the medicament container during operation. When a collapsible container is utilized to accommodate shrinking of volume of the medicament reservoir, the materials of construction do not satisfactorily inhibit the permeation of air through the container walls to provide a desired long term use in storage of the device without compromise of the stored medicament.

The present invention overcomes the shortcomings of the prior art devices by providing nozzle and medicament reservoir combination which enables multiple dose delivery of a preservative-free product with accurate dose dispensing over extended periods of time.

SUMMARY OF THE INVENTION

Apparatus in accordance with the present invention for instilling a medicament to an eye generally includes a rigid housing which provides a means for containing the reservoir medicament. The rigid housing can be formed from materials which prevent any permeation of medicament or the air therethrough.

A nozzle provides a means for instilling a dose of the medicament into an eye and displacement means, sealing a front end of the rigid housing and in fluid communication with the reservoir, is provided for metering doses of the medicament from the reservoir to the nozzle and for forcing each metered dose through the nozzle.

A stopper, slidably disposed within a rear end of the rigid housing means, provides a means for gradually decreasing a housing volume containing the medicament. This prevents the development of a detrimental amount of residual vacuum within the housing due to removal of medicament therefrom. The stopper prevents such vacuum creation within the housing by sliding within the housing under the force of atmospheric pressure.

Additionally, the displacement means comprises a positive displacement pump within the pump head with an angular skirt valve disposed within the pump body. Importantly, the pump body is integrally molded as part of the housing means front end to further reduce the number of separate parts and provide for more efficient manufacturing of the apparatus.

The pump body comprises a tapered cylinder means for enveloping the pump head with the tapered cylinder means being in fluid communication with the reservoir. Tapered cylinder means protects the skirt valve and breaks up air bubbles, if any. This accordingly improves pump efficiency. In addition, the pump further comprises a collapsible boot having a rear portion fitted to an exterior of the housing means front end and the front portion forming a flexible nozzle outer sleeve. This provides a microbial barrier and requires no further mechanical closures.

The nozzle includes a piston with a rear portion attached to the pump head and a front portion fitted through the nozzle outer sleeve and establishing in it interface therebetween. The piston is movable with the pump and the nozzle includes channel means, disposed within the piston, for conducting each metered amount of medicament from the pump head to the interface, each metered amount of medicament exiting the nozzle means through the interface.

In addition, spring means disposed around the piston and beneath the boot are provided for moving the pump head and piston forwardly after compression thereof. The forward movement causes the pump head angular skirt valve to force the metered amount of medicament from the tapered cylinder into the channel means.

Diaphragm means, disposed in the stopper, may be provided for accommodating transient decreases in the volume containing the medicament reservoir during metering of doses therefrom by said displacement means. In addition, the diaphragm means reduces agitation in the reservoir during metering doses therefrom by the displacement means. It is important to minimize backward movement of the stopper in the medicament reservoir during the transfer of metered amounts of medicament from the reservoir to the nozzle in order to ensure accurate metering of doses.

More particularly, the diaphragm means comprises means for minimizing dead space and trapped air in the reservoir during insertion of the stopper means into the rigid housing. This is particularly important in manufacture of the apparatus whereby the reservoir is filled and capped while under vacuum to prevent bubbles which cause inaccuracies in the metering of doses from the reservoir.

BRIEF DESCRIPTION OF THE DRAWINGS

The advantages and features of the present invention will be better understood by the following description when considered in conjunction with the accompanying drawings in which:

FIG. 1 is a plan view of apparatus in accordance with the present invention for instilling a medicament into an eye;

FIG. 2 is a cross section of the apparatus shown in FIG. 1 generally showing a rigid housing, a nozzle, a positive displacement pump in a "cocked" position, a sliding stopper within the rigid container along with a diaphragm.

DETAILED DESCRIPTION

Figure 3:
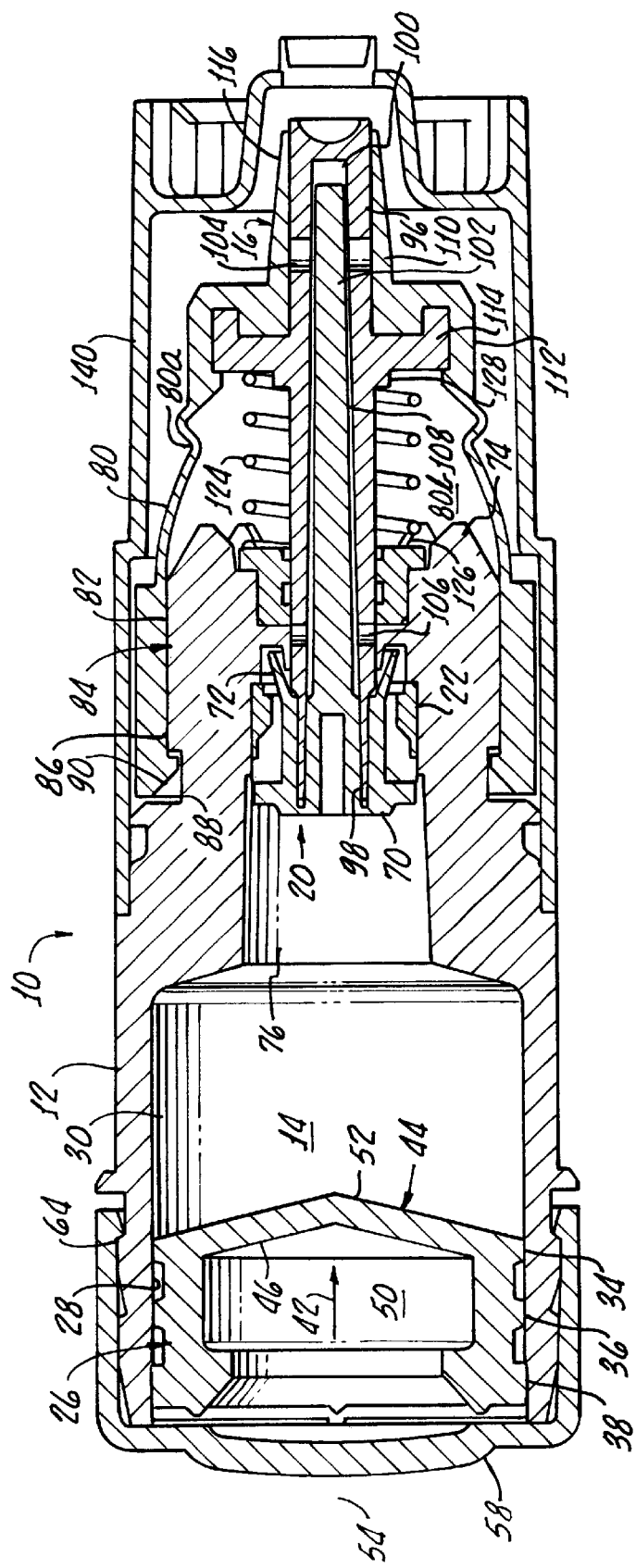
FIG. 3 is similar to FIG. 2 with the positive displacement pump in a "discharged" position for transferring a metered dose of medicament from the reservoir and through the nozzle.

With reference to FIG. 1, there is shown apparatus 10 in accordance with the present invention for instilling a medicament (not shown) into an eye (not shown). In general, the apparatus includes a rigid housing 12 which provides a means for containing a reservoir 14 of the medicament, see FIGS. 2 and 3, and a nozzle 16 which provides a means for instilling a dose (not shown) of the medicament into an eye.

The housing 12 is made from an air impermeable material, such as high density, polyethylene (HDPE) which may be formed by injection molding. The impermeable characteristic of the HDPE prevents any migration of air into the reservoir 14, or migration of the medicament outwardly from the reservoir 14. Other suitable materials for the housing include, but are not limited to, Glass (Various), TPX®, Polypropylene, Polycarbonate, LDPE (Low Density Polyethylene), Polystyrene, ULTEM®, BAREX®, Polyester (Pctg, Petg), Plastic Coated Metals, PBT, Teflon® Blends, ABS, LLDPE, Aluminum and Stainless Steel(s), DELRIN®, UHMWPE (Ultra-High molecular weight polyethylene, or nylon).

Alternatively, a base material with a coating such as SARAN® or ACLAR® may be utilized.

Displacement, or reciprocating pump means 20 seals a front end 22 of the housing 14 and is in fluid communication with the reservoir 14 for metering doses of medicament from the reservoir 14 through the nozzle 16, as will be hereinafter discussed in greater detail.

Importantly, the pump means 20, while in fluid communication with the reservoir 14 is not engulfed in or surrounded by the medicament, but rather disposed at the housing front end 22, for withdrawn medicament from the reservoir 14. This is crucial to the design because the pump 20 cannot function efficiently when air is present.

It should be apparent that, while doses of medicament are removed from the reservoir 14, both transient and long term pressure differentials occur within the housing 12, which must be accommodated for, in order to reliably instill accurate metered doses of medicament into an eye.

In the present invention, stopper means 26 slidably disposed within the housing 12 at a rear end 28 accommodates for long term pressure differentials by gradually decreasing a housing volume containing the medicament reservoir 14.

As hereinabove noted, the housing 14 may be formed from a high density polyethylene (HDPE) which is injection moldable and is highly impermeable to air outside the apparatus 10 and medicament disposed in the reservoir 14. The housing includes a smooth inside barrel 30 including the rear end 28 which is smooth for enabling the stopper means 26, which preferably is formed from a suitable rubber or elastomeric material. Redundant microbial seals 34, 36, 38, not only provide for a dynamic microbial barrier to the medicament, but also prevents any moisture loss.

As medicament is withdrawn from the reservoir 14, the stopper means 26 moves in a direction indicated by the arrow 42 to reduce the reservoir 14 volume and accordingly prevent any significant vacuum buildup within the housing 12. Thus, the stopper means serves as an accommodating member to alternate pressure fluctuations inside the reservoir 14, which otherwise could cause or result in leaks, cavitation or displacement pump 20 malfunction.

Diaphragm means 44 may be utilized which provide for accommodating transient decreases in the volume containing a medicament reservoir 14 during metering of doses therefrom by the displacement means 20.

When used, diaphragm means 44 is preferably formed in a front end 46 of the stopper 26. In operation, abrupt removal of metered doses from the reservoir is instantaneously accommodated by flexure of the diaphragm 44 in the direction of the arrow 42, the diaphragm being made of suitable thickness to provide the response required. Thereafter, the stopper 26 gradually moves in the direction of the arrow 42 to provide long term reduction in the medicament reservoir 14 volume. Transient movement of the diaphragm 44 is enabled by a hollow cavity 50 therebehind and within the stopper 26.

The angular face 52 of the diaphragm 44 provides a means for minimizing dead space and trapped air in the reservoir 14 during insertion of the stopper means 26 into the rigid housing 12. Preferably, the diaphragm 44 includes approximately a 150° included angle at a centerline 54 of the stopper and apparatus 10. The angulated diaphragm 44, when inserted into the reservoir 14, reduces, or helps to eliminate dead space and trapped air.

After filling the reservoir 14 and insertion of the stopper means 26, an end cap 58 may be attached to the rear end 28 of the housing 26 around an outside surface 60 by a latch arrangement 64. End cap 58 must allow fast flow of air to the top of stopper 26. The pump 20 includes a pump head 70 with an annular skirt valve 72 disposed within a pump body 74. For economy of manufacture, the pump body 74 is molded as one piece with the housing 12.

The pump head 70 is disposed within a narrow, tapered cylinder 76 which envelops the piston head 70 and protects the skirt valve 72 from any damage. Further, the narrow, tapered cylinder 76 functions to break up any undesirable air bubbles. The pump head 70 along with the skirt valve 72 may be formed from any suitable plastic material, as is well known in the art.

The pump 20 includes a collapsible boot, or bellows, 80 fitted to an exterior surface 82 of a front end 84 of the housing 12 to form a compression seal 86 which provides a microbial barrier which requires no mechanical closure. A single inflection 80a in the boot bellows 80 enables smooth bucking of the boot bellows 80 during activation. This structure provides for a rise in pressure in a boot bellows chamber 80b to be less than one-third (⅓) of the seal 86 capacity. Hence, a microbial barrier is maintained during activation.

A groove 88 formed in the front end 84 of the housing 12 captures a depending portion 90 of the boot 80 to prevent longitudinal slipping between the boot 80 and the housing front end 84. This structure also provides positive mechanical registration to resist buckling forces during firing of the nozzle 16. The boot 80 may be formed from any suitable material such as Dynaflex® of appropriate thicknesses.

The nozzle 16 includes a relatively hard piston 96 with a rear portion 98 attached to the pump head 70 and includes a cavity 100 for accommodating a forward portion 102 to the pump head 70.

Subtending cavities 104, 106 provide a means for accommodating the metered amount of medicament and a channel 108 established between the piston 96 and the pump head forward portion 102 enables a metered dose of medicament to be forced by the skirt valve 72 as the pump head moves forward, as indicated in FIG. 2, to be forced out of the nozzle 16 between an interface 116 established between the piston 96 and a relatively soft outer sleeve 110, the piston 96 being made from HOSTALEN® or other HDPE plastic and outer sleeve 110 being made from any suitable elastomer or thermo plastic elastomer TPE material, such as Dynaflex®.

This operation can be seen by comparing FIGS. 2 and 3 in which FIG. 2 shows the apparatus 10 in a "cocked" position, with the skirt valve 72 in a setback position in which forward movement upon release from "cocked" position then traps the dose of medicament and removes same from the reservoir 14 along the channel 108 and through the interface 116 as hereinabove described and indicated by arrows 120, 122 in FIG. 2.

It should be appreciated that upon movement, the skirt valve 72 creates a vacuum in the cavity 100 thereby drawing liquid thereinto to "charge" the cavity 100 prior to releae or firing from the "cocked" position.

Preferably, the boot 80 and sleeve 110 are integrally formed. Accordingly, a seal 112 is formed between a radially extending portion 114 of the piston 96.

The pump 20 includes spring means 124, disposed around the piston 96 and beneath the boot 80, for causing the pump head 70 and piston 96 to move forwardly. A guide angle 126 allows the spring 124 to self locate during high speed assembly. A shoulder 128 provides radial registration of the spring 124 on the piston 96 and in turn the spring 124 ensures proper seating of the elastomeric front seal 130.

As hereinabove noted, the forward movement causes the pump head angular skirt valve 72 to force the immediate amount of medicament from the tapered cylinder 76 portion of the reservoir 14 into the channel 108.

The seal 130 removes communication of the pump body 74, collapsible bellows 80, drive spring 124 and nozzle 16 from the reservoir 14.

It is important to appreciate that there is no communication between the pump body 74, boot 80, drive spring 124 with the medicament reservoir 14. This is important because the pump 20 cannot function efficiently when air is present. Because the spring 124 is not in contact with the medicament, the use of a metal spring is enabled which provides for consistent performance which would be impossible through the use of a costly and inconsistent plastic or elastomer spring which would be required if there was communication between the medicament and the spring.

When not in use, the nozzle 16 may be covered by a plastic cap 128 removably attached to the housing 12.

Although there has been hereinabove described a specific apparatus for instilling a medicament into an eye for the purpose of illustrating the manner in which the invention is used to advantage, it should be appreciated that the invention is not limited thereto. Accordingly, any and all modifications, variations, equivalent arrangements which may occur to those skilled in the art, should be considered to be within the scope of the invention as defined in the appended claims.

What is claimed is:

1. Apparatus for instilling a medicament into an eye, said apparatus comprising:
a medicament;
rigid housing means containing a reservoir of the medicament;
nozzle means for instilling a dose of the medicament into an eye;
displacement means, sealing a front end of said rigid housing means and in fluid communication with said reservoir, for metering doses of medicament from said reservoir to said nozzle means and for forcing each metered dose through said nozzle means; and
stopper means, slidably disposed within a rear end of said rigid housing means, for gradually decreasing a housing volume containing the medicament reservoir.

2. The apparatus according to claim 1 wherein said displacement means comprises a positive displacement pump having a pump head with an annular skirt valve disposed within a pump body, said pump body being integrally molded as part of the rigid housing means front end.

3. The apparatus according to claim 2 wherein said pump body comprises tapered cylinder means for enveloping said pump head, said tapered cylinder means being in fluid communication with said reservoir.

4. The apparatus according to claim 3 wherein the pump further comprises a collapsible boot having a rear portion fitted to an exterior of the housing means front end and a front portion forming a flexible nozzle outer sleeve.

5. The apparatus according to claim 4 wherein said nozzle means includes a piston with a rear portion attached to said pump head, and movable therewith, and a front portion fitted through the nozzle outer sleeve and establishing an interface therebetween.

6. The apparatus according to claim 5 wherein said nozzle means includes channel means, disposed within said piston, for conducting each metered amount of medicament from said pump head to said interface, each metered amount of medicament exiting the nozzle means through said interface.

7. The apparatus according to claim 6 wherein the pump further comprises spring means disposed around said piston and beneath said boot for moving said pump head and piston forwardly after compression thereof, the forward movement causing the pump head annular skirt valve to force the metered amount of medicament from the tapered cylinder means into said channel means.

8. The apparatus according to claim 7 wherein said spring means is formed from metal.

9. The apparatus according to claim 8 wherein said rigid housing means is formed from a material selected from a group comprising HDPE, Glass, TPX, Polypropylene, Polycarbonate, LDPE, Polystyrene, ULTEM®, BAREX®, Polyester, Plastic Coated Metal, PBT, Teflon Blends, ABS, LLDPE, Aluminum, Stainless Steel, SARAN®, ACLAR®, Nylon, DELRIN®, and Ultra-High Molecular Weight Polyethylene.

10. The apparatus according to claim 1 further comprises means for minimizing dead space and trapped air in said reservoir during insertion of said stopper means into said rigid housing means.

11. The apparatus according to claim 10 further comprising diaphragm means for accommodating transient decreases in the volume contained in the reservoir during metering of doses therefrom by said displacement means.

12. The apparatus according to claim 11 wherein said diaphragm means is disposed in said stopper means.

13. The apparatus according to claim 12 wherein said means for minimizing dead space and trapped air comprises an angular face formed into said diaphragm means, said angular face being in contact with the reservoir of medicament.

14. Apparatus for instilling a medicament into an eye, the apparatus comprising:
a medicament;
rigid housing means containing a reservoir of the medicament;
displacement means, sealing a front end of said rigid housing means and in fluid communication with said reservoir, for metering doses of medicament from said reservoir to a nozzle means and for forcing each metered dose through said nozzle means; and stopper means, slidably disposed within a rear end of said rigid housing means, for preventing vacuum creation within said rigid housing means due to metering of doses from said reservoir, said stopper means sliding within said rigid housing means under the force of atmospheric pressure.

15. The apparatus according to claim 14 wherein said displacement means comprises a positive displacement pump having a pump head with an annular skirt valve disposed within a pump body, said pump body being integrally molded as part of the rigid a housing means front end.

16. The apparatus according to claim 15 wherein said pump body comprises tapered cylinder means for enveloping said pump head, said tapered cylinder means being in fluid communication with said reservoir.

17. The apparatus according to claim 16 wherein the pump further comprises a collapsible boot having a rear portion fitted to an exterior of the rigid housing means front end and a front portion forming a flexible nozzle outer sleeve.

18. The apparatus according to claim 17 wherein said nozzle means includes a piston with a rear portion attached to said pump head, and movable therewith, and a front portion fitted through the nozzle outer sleeve and establishing an interface therebetween.

19. The apparatus according to claim 18 wherein said nozzle means includes channel means, disposed within said piston, for conducting each metered amount of medicament from said pump head to said interface, each metered amount of medicament exiting the nozzle means through said interface.

20. The apparatus according to claim 19 wherein the pump further comprises spring means disposed around said piston and beneath said boot for moving said pump head and piston forwardly after compression thereof, the forward movement causing the pump head annular skirt valve to force the metered amount of medicament from the tapered cylinder means into said channel means.

21. The apparatus according to claim 20 wherein said spring is formed from metal.

22. The apparatus according to claim 21 wherein said rigid housing means is formed from a material selected from a group comprising HDPE, Glass, TPX, Polypropylene, Polycarbonate, LDPE, Polystyrene, ULTEM, BAREX, Polyester, Plastic Coated Metal, PBT, Teflon Blends, ABS, LLDPE, Aluminum, Stainless Steel, SARAN, ACLAR, Nylon, DELRIN, and Ultra-High Molecular Weight Polyethylene.

23. The apparatus according to claim 11 further comprising means for minimizing dead space and trapped air in said reservoir during insertion of said stopper means into said rigid housing means.

24. The apparatus according to claim 23 further comprising diaphragm means, disposed in said stopper means, for reducing agitation and transient pressure changes in said reservoir during metering of doses therefrom by said displacement means.

25. The apparatus according to claim 24 wherein said means for minimizing dead space and trapped air comprises an angular face formed into said diaphragm means, said angular face being in contact with the reservoir of medicament.

26. Apparatus for instilling a medicament into an eye, the apparatus comprising:

a medicament;

rigid housing means containing a reservoir of the medicament;

nozzle means for instilling a metered amount of the medicament from the reservoir into an eye;

reciprocating means, disposed in a front end of said housing means and in fluid communication with said reservoir, for transferring metered amounts of medicament from the reservoir to said nozzle means and for forcing each metered amount of medicament through said nozzle means;

stopper means, slidably disposed within a rear end of said rigid housing means, for preventing vacuum creation within said rigid housing means due to metering of doses from said reservoir, said stopper means sliding within said rigid housing means under the force of atmospheric pressure.

27. The apparatus according to claim 26 wherein said reciprocating means comprises a positive displacement pump having a pump head with an annular skirt valve disposed within a pump body, said pump body being integrally molded as part of the housing means front end.

28. The apparatus according to claim 27 wherein said pump body comprises tapered cylinder means for enveloping said pump head, said tapered cylinder means being in fluid communication with said reservoir.

29. The apparatus according to claim 28 wherein the pump further comprises a collapsible boot having a rear portion fitted to an exterior of the housing means front end and a front portion forming a flexible nozzle outer sleeve.

30. The apparatus according to claim 29 wherein said nozzle means includes a piston with a rear portion attached to said pump head, and movable therewith, and a front portion feed through the nozzle outer sleeve and establishing an interface therebetween.

31. The apparatus according to claim 30 wherein said nozzle means includes channel means, disposed within said piston, for conducting each metered amount of medicament from said pump head to said interface, each metered amount of medicament exiting the nozzle means through said interface.

32. The apparatus according to claim 31 wherein the pump further comprises spring means disposed around said piston and beneath said boot for moving said pump head and piston forwardly after compression thereof, the forward movement causing the pump head annular skirt valve to force the metered amount of medicament from the tapered cylinder means into said channel means.

33. The apparatus according to claim 32 wherein said spring means is formed from metal.

34. The apparatus according to claim 33 wherein said rigid housing means is formed from a material selected from a group comprising HDPE.

35. The apparatus according to claim 32 further comprising means for minimizing dead space and trapped air in said reservoir during insertion of said stopper means into said rigid housing means.

36. The apparatus according to claim 35 further comprising diaphragm means, disposed in said stopper means, for reducing agitation and transient pressure changes in said reservoir during metering of doses therefrom by said displacement means.

37. The apparatus according to claim 36 wherein said means for minimizing dead space and trapped air comprises an angular force formed into said diaphragm means, said angular force being in contact with the reservoir of medicament.

* * * * *